United States Patent [19]

Hunt et al.

[11] Patent Number: 4,866,051

[45] Date of Patent: Sep. 12, 1989

[54] MICRONISED BECLOMETHASONE DIPROPIONATE MONOHYDRATE COMPOSITIONS AND METHODS OF USE

[75] Inventors: John H. Hunt, Hertford; John M. Padfield, Meldreth, both of England

[73] Assignee: Glaxo Group Limited, London, England

[21] Appl. No.: 696,427

[22] Filed: Jan. 30, 1985

Related U.S. Application Data

[63] Continuation of Ser. No. 532,003, Sep. 14, 1983, abandoned, which is a continuation of Ser. No. 433,704, Oct. 12, 1982, abandoned.

[30] Foreign Application Priority Data

Oct. 19, 1981 [GB] United Kingdom ............ 131425

[51] Int. Cl.$^4$ ........................................ A61K 31/56
[52] U.S. Cl. ........................................ 514/180; 514/826
[58] Field of Search ............... 260/397.45; 424/243; 514/180

[56] References Cited

U.S. PATENT DOCUMENTS

| | | | |
|---|---|---|---|
| 4,347,236 | 8/1982 | Tanskanen | 424/243 |
| 4,364,923 | 12/1982 | Cook et al. | 424/243 |
| 4,370,322 | 1/1983 | Busse et al. | 424/243 |
| 4,391,755 | 7/1983 | Wang et al. | 260/397.45 |

FOREIGN PATENT DOCUMENTS

| | | | |
|---|---|---|---|
| 61637 | 3/1974 | Portugal | 260/397.45 |
| 71309 | 5/1980 | Portugal | 260/397.45 |
| 1047519 | 11/1966 | United Kingdom | 260/397.45 |
| 1511820 | 5/1978 | United Kingdom | 260/397.45 |

OTHER PUBLICATIONS

Acta Crystallographica (1981), B.37, 383–387, W. L. Duax et al.

The Theory and Practice of Industrial Pharmacy, Leon Lachman, Herbet A. Liebermann and J. L. Karug, (1976), p. 279.

*Primary Examiner*—Douglas W. Robinson
*Assistant Examiner*—Joseph A. Lipovsky
*Attorney, Agent, or Firm*—Bacon & Thomas

[57] ABSTRACT

Beclomethasone dipropionate in the form of its micronised monohydrate substantially free from water other than water of crystallisation. Pharmaceutical compositions containing the compound are also described. The compositions may be in the form of powder inhalation cartridges especially suitable for the treatment and/or prophylaxis of asthma.

9 Claims, 1 Drawing Sheet

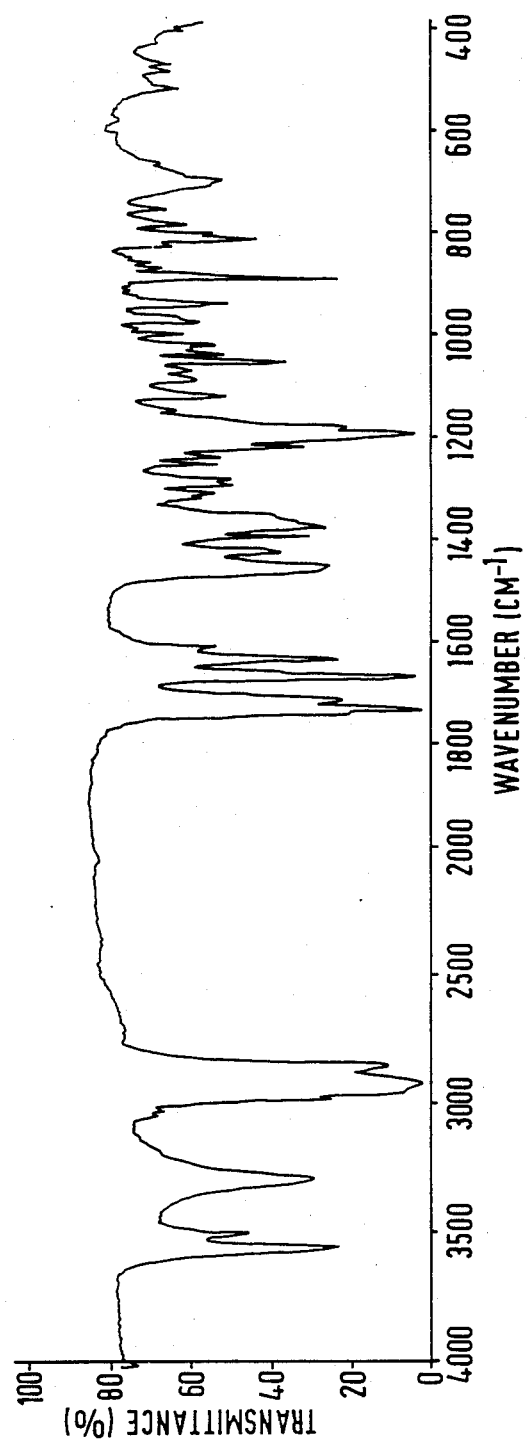

MICRONISED BECLOMETHASONE DIPROPIONATE MONOHYDRATE COMPOSITIONS AND METHODS OF USE

This application is a continuation of application Ser. No. 532,003, filed Sept. 14, 1983, now abandoned; which is a continuation of Ser. No. 433,704, filed Oct. 12, 1982, also abandoned.

This invention relates to improvements in or relating to pharmaceutical compositions comprising 9α-chloro-11β-hydroxy-16β-methyl-17α,21-dipropionyloxypregna-1,4-diene-3,20-dione, which is known as beclomethasone dipropionate.

Beclomethasone dipropionate is a corticosteroid which exhibits a high topical antiinflammatory activity, and is described and claimed in U.K. patent specification No. 1,047,519. The compound may be formulated into preparations suitable for topical administration as, for example, lotions, creams, oitments and the like. In the management of asthma it has been found effective to spray the corticosteroid into the bronchial system prophylactically. Formulations containing beclomethasone dipropionate for the treatment of asthma include aerosol formulations consisting of a suspension of the micronised corticosteroid in a chlorofluorohydrocarbon propellant. Such formulations are dispensed using conventional pressurised aerosols or inhalers.

It has been found, however, that when micronised beclomethasone dipropionate is formulated with aerosol propellants, the active compound exhibits crystal growth which results in the formation of particles having a size above 20 μm. Medicaments for administration by inhalation desirably have a controlled particle size. The optimum particle size for inhalation into the bronchial system is usually 1-10 μm preferably 2-5 μm. Particles having a size above 20 μm are generally too large when inhaled to reach the small airways. U.K. patent specification No. 1429184 describes a method of converting an anti-inflammatory steroid, such as beclomethasone dipropionate, exhibiting crystal growth in aerosol propellants, into a form which does not exhibit such growth, whereby the steroid is contacted with a halogenated hydrocarbon to form a crystalline solvate therewith, the crystalline material so formed being reduced to a particle size permitting inhalation into the human bronchial system when dispersed as an aerosol.

Similarly, German Offenlegungsschrift 3018550 describes ethyl acetate solvates of antiinflammatory steroids (particularly beclomethasone dipropionate) and South African Patent Specification No. 80/2601 describes solvates of beclomethasone dipropionate with alkanes having from 5 to 8 carbon atoms, both for use in aerosol formulations. All these solvates appear to have essentially the same type of crystal structure.

An alternative inhalation form of beclomethasone dipropionate is a form suitable for powder inhalation especially valuable for treating patients who are unable to use the pressurised inhalers effectively or who might use them incorrectly. In this form the contents of a cartridge are inhaled using an inhalation device which releases the drug from the cartridge when the patient inhales. Such drug delivery systems are more reliable for many patients.

We have found that when pharmaceutical powder compositions which contain beclomethasone dipropionate contained in conventional gelatin inhalation cartridges are stored in adverse conditions the particle size distribution of the powder changes. Thus the fraction of fine particles having the desired 1-10 μm size may decrease to such an extent that an unsatisfactory product may result.

We have now found that in pharmaceutical dry powder compositions for use in powder inhalation cartridges, the above problem can be overcome by using beclomethasone dipropionate in the form of its monohydrate. We have found that the particle size of the micronised monohydrate in such powder compositions remains substantially constant even after storage for extended periods. Beclomethasone dipropionate monohydrate, which differs in its crystal structure from the previously described solvates referred to above, has never been proposed for use in powder formulations for bronchial inhalation.

According to one aspect of the invention we provide beclomethasone dipropionate monohydrate substantially free from water other than water of crystallisation, at least 90% by weight of the particles thereof having an effective particle size below 10 μm, preferably between 2-5 μm.

The new monohydrate of the invention has also been characterised by its infrared spectrum. The infrared spectrum of a sample of the monohydrate as a mull in mineral oil is shown in the FIGURE of the accompanying drawing.

The principal absorption bands are at 3560, 3510, 3300, 1730, 1710, 1663, 1630, 1285, 1190, 1120, 1090, 1053, 973, 940, 890, 810, 785, and 700 $cm^{-1}$.

The invention further provides a pharmaceutical dry powder composition comprising micronised beclomethasone dipropionate monohydrate in association with at least one pharmaceutically acceptable powder carrier or excipient.

The monohydrate may be conventionally prepared by crystallisation from a mixed solvent system consisting of water and a water-miscible organic solvent. For example, the monohydrate may be prepared by slowly adding a solution of beclomethasone dipropionate in a water-miscible organic solvent to water, whereafter the monohydrate is crystallised. The beclomethasone dipropionate is conveniently first dissolved in the organic solvent at an elevated temperature e.g. at a temperature of rom 40° to 80° C., for example, at about 60° C. The organic solvent solution is then added slowly to water, preferably with stirring, while maintaining the solution at a temperature of e.g. 40° to 80° C., preferably about 60° C. Upon cooling, of the resulting suspension, the crystalline monohydrate is formed.

Water-miscible organic solvents which may be used in such a process include, for example, methanol, ethanol, acetone and dioxan.

After crystallisation, the monohydrate may be isolated by, for example, filtration and washed and dried in conventional manner. For example, the monohydrate may be dried by air drying, drying under reduced pressure, or drying in the presence of a sterile inert gas.

The beclomethasone dipropionate monohydrate may be micronised to the desired particle size range by conventional techniques, for example using a ball mill or fluid energy mill or by ultrasonic means. The desired fraction may be separated out by air classification or sieving. The compositions may be prepared by intimately mixing the ingredients together, for example, in a high shear fluidising mixer. The compositions according to the invention may conveniently be filled into gelatin, plastics or other capsules. Such capsules may be conventional two-part capsules or may be sealed. In general, No. 3 size hard gelatin two-part capsules are preferred.

The monohydrate may also be prepared by comminuting beclomethasone dipropionate in the presence of water, for example, in a ball mill or by ultrasonic means.

The compositions according to the invention exhibit the high topical antiinflammatory activity of beclomethasone dipropionate. As indicated above, we have found that the particle size of the crystalline monohydrate remains substantially constant even after storage for extended periods.

These properties render the monohydrate of value in the preparation of the pharmaceutical powder compositions and their packaging in containers or packs.

The compositions according to the invention are conveniently in the form of inhalation cartridges which may be used with an inhalation device, for example that described in U.K. Pat. No. 1561835 or British patent application No. 80 39174 (Publication No. 2064336).

For use in the pharmaceutical powder compositions such as inhalation cartridges, the monohydrate is micronised, preferably such that at least 90% by weight of the particles have an effective particle size below 10 $\mu$m and preferably between 2 to 5 $\mu$m. Thus in a preferred embodiment we provide pharmaceutical powder compositions such as inhalation cartridges, which comprise micronised beclomethasone dipropionate monohydrate, in which at least 90% by weight of the particles have an effective particle size below 10 $\mu$m, preferably between 2–5 $\mu$m, and at least one pharmaceutically acceptable dry powder carrier or excipient. The carrier may be selected from diluents such as, for example, lactose, mannitol, arabinose or dextrose, but is preferably lactose. The carrier or excipient may be commercially available in the desired particle size range or may also be separated by air classification or sieving. The compositions may also additionally contain a bronchodilator such as isoprenaline or salbutamol or an anticholinergic such as atropine or a drug used in the prophylaxis of allergic conditions such as sodium cromoglycate.

The amount of the composition contained in the capsule will to some extent depend on the desired dosage.

The compositions are conveniently in the form of dosage units (e.g. inhalation cartridges) containing beclomethasone dipropionate monohydrate equivalent to from 10–1000 $\mu$g and preferably from 50–500 $\mu$g (e.g. 20–250 $\mu$g) of beclomethasone dipropionate and from 10–100 mg by weight and more especially from 25–50 mg by weight of the carrier. Most preferably unit dosages of the compositions are such as to provide 100 to 300 $\mu$g usually 200 $\mu$g of beclomethasone dipropionate.

The average daily dosage of beclomethasone dipropionate monohydrate will depend on the age, weight and condition of the patient to be treated. In general, average daily dosages lie in the range of 200 to 2000 $\mu$g, preferably 400 to 800 $\mu$g, of beclomethasone dipropionate. In the case of high dosage compositions, the daily dosage can be approximately about 4 mg of beclomethasone dipropionate.

The invention will now be illustrated with reference to the following non-limiting Examples. All temperatures are in °C. "Hplc" is high-pressure liquid chromatography, and "gc" is gas chromatography.

EXAMPLE 1

Beclomethasone dipropionate (0.5 g), which had been previously dried to constant weight at 100°, was dissolved in 15 ml ethanol. Water (100 ml) was added, with stirring, causing clouding followed by crystallisation. The crystalline hydrate in the form of long thin laths was removed by filtration and air-dried. Yield 0.5 g.

The sample had the IR spectrum indicated in the FIGURE of the accompanying drawing.

The crystals were subsequently micronised in a fluid energy mill to the particle size 2–5 $\mu$m.

EXAMPLE 2

Beclomethasone dipropionate (550 g) was dissolved in 3.2 liters of hot methanol and filtered. The filtrate held at a temperature of about 60° was added with stirring to 33 liters of deionised water, also at 60°. The mixture was cooled to 20° and the resulting crystalline monohydrate was removed by filtration, washed with water (1.0 liter) and air-dried. Yield 506 g.

| Analytical data Beclomethasone dipropionate | | |
|---|---|---|
| (hplc) | 96.4% | w/w |
| Water (gc) | 3.8% | w/w |
| Loss on drying (105°) | 3.5% | w/w |

The sample had the I.R. spectrum shown in the FIGURE of the accompanying drawing.

The crystals were subsequently micronised in a fluid energy mill to the particle size 2–5 $\mu$m.

EXAMPLE 3

Beclomethasone dipropionate (0.5 g) and water (25 ml) were ball milled for 36 hours in a glass bottle with steatite balls. The solid in the form of fine particles of 2–5 $\mu$m size was removed by filtration and air dried to give the monohydrate with the I.R. spectrum shown in the FIGURE of the accompanying drawing.

EXAMPLE 4

Deionised water (16.5 l) was heated to 60° and beclomethasone dipropionate (250 g) dissolved in hot methanol (1.6 l) was added slowly at about 60° over a period of 2.5 minutes with stirring. The mixture was cooled to room temperature to give the precipitated hydrate which was collected by filtration, washed with water and dried in vacuo (ca 150 mmHg/40°). The product (253 g) had the I.R. spectrum indicated in the FIGURE. Loss on drying (105°) 3.19% w/w.

The crystals were subsequently micronised in a fluid energy mill to the particle size 2–5 $\mu$m.

EXAMPLE 5

Beclomethasone dipropionate monohydrate: inhalation cartridges for use in a powder inhalation device

| | Per cartridge |
|---|---|
| Beclomethasone dipropionate monohydrate, micronised | 114 or 228 $\mu$g |
| Lactose | to 25 mg. |

The active ingredient and lactose are intimately mixed in a high shear fluidising mixer. The blend is encapsulated in No. 3 size hard gelatin capsules using an automatic machine. Each cartridge contains the equivalent of 110 μg or 220 μg of beclomethasone dipropionate.

EXAMPLE 6

Beclomethasone dipropionate monohydrate and salbutamol: inhalation cartridges for use in a powder inhalation device

|  | Per cartridge |
|---|---|
| Beclomethasone dipropionate monohydrate, micronised | 228 μg |
| Salbutamol sulphate, micronised | 528 μg |
| Lactose | to 25 mg |

The active ingredients and lactose are intimately mixed as before and the blend is encapsulated in No. 3 size hard gelatin capsules using an automatic machine. Each cartridge contains the equivalent of 220 μg of beclomethasone dipropionate and 440 μg of salbutamol.

We claim:

1. A pharmaceutical dry powder composition comprising micronised beclomethasone dipropionate monohydrate in association with at least one pharmaceutically acceptable dry powder carrier or excipient.

2. A composition according to claim 1 wherein at least 90% by weight of the micronised beclomethasone dipropionate monohydrate has an effective particle size below 10 μm.

3. A composition according to claim 2 wherein at least 90% by weight of the micronised beclomethasone dipropionate monohydrate has an effective particle size between 2 to 5 μm.

4. A composition according to claim 1 in the form of a dosage unit comprising a powder inhalation cartridge containing beclomethasone diproprionate monohydrate equivalent to from 10 to 1000 μg of beclomethasone dipropionate.

5. A composition according to claim 4 wherein the dosage unit contains beclomethasone dipropionate monohydrate equivalent to from 50 to 500 μg of beclomethasone dipropionate.

6. A composition according to claim 1 additionally containing at least one compound selected from the group consisting of salbutamol and sodium cromoglycate.

7. A pharmaceutical composition as claimed in claim 1 in association with a powder inhalation device.

8. A powder inhalation device containing a pharmaceutical composition as defined in claim 1.

9. A method of treating bronchial conditions in a subject which comprises administering to said subject by inhalation techniques an effective amount of micronised beclomethasone dipropionate monohydrate in a pharmaceutical dry powder composition.

* * * * *